(12) United States Patent
Symonds et al.

(10) Patent No.: US 7,520,924 B2
(45) Date of Patent: Apr. 21, 2009

(54) APPARATUS FOR COLLECTING PARTICLES

(75) Inventors: William Hunter Symonds, Salisbury (GB); David James Squirrell, Salisbury (GB); Nigel Patrick Pomeroy, Salisbury (GB); Martin John Berry, Salisbury (GB)

(73) Assignee: The Secretary of State for Defence (GB)

( * ) Notice: Subject to any disclaimer, the term of this patent is extended or adjusted under 35 U.S.C. 154(b) by 590 days.

(21) Appl. No.: 10/542,676

(22) PCT Filed: Jan. 21, 2004

(86) PCT No.: PCT/GB2004/000251

§ 371 (c)(1),
(2), (4) Date: Jul. 19, 2005

(87) PCT Pub. No.: WO2004/065017

PCT Pub. Date: Aug. 5, 2004

(65) Prior Publication Data

US 2006/0123752 A1    Jun. 15, 2006

(30) Foreign Application Priority Data

Jan. 21, 2003    (GB)    ................... 0301257.2

(51) Int. Cl.
*B01D 45/00*    (2006.01)
(52) U.S. Cl. ................ 96/413; 55/434.4; 55/459.1; 55/434.2; 73/863.12; 73/863.21; 96/372; 96/420
(58) Field of Classification Search ............... 55/434.2, 55/459.1; 73/863.12, 863.21; 95/14, 18, 95/271; 96/413, 420
See application file for complete search history.

(56) References Cited

U.S. PATENT DOCUMENTS

| | | | |
|---|---|---|---|
| 1,971,387 A | | 8/1934 | Scoville |
| 3,780,567 A | * | 12/1973 | Ovard ................. 73/863.21 |
| 4,324,146 A | * | 4/1982 | Born .................. 73/863.12 |

(Continued)

FOREIGN PATENT DOCUMENTS

CH    251108    10/1947

(Continued)

OTHER PUBLICATIONS

Abstract of Japanese Patent Document No. 63224754 (Sep. 19, 1988).

(Continued)

*Primary Examiner*—Duane S Smith
*Assistant Examiner*—Sonji Turner
(74) *Attorney, Agent, or Firm*—Dean W. Russell; Kilpatrick Stockton LLP (57) ABSTRACT

Improved apparatus for collecting particles from air comprises a cyclone having air inlet and outlet means, means maintaining an airflow there through and means delivering a collecting fluid from a reservoir to particles separated from the air flow in the cyclone, in which the air inlet means is associated with means for heating the incoming air. The apparatus, which is optionally provided with enclosure means for trapping heat, prevents freezing of the collecting fluid at temperatures near to and even below 0° C.

11 Claims, 5 Drawing Sheets

U.S. PATENT DOCUMENTS

| | | | |
|---|---|---|---|
| 6,184,517 B1 * | 2/2001 | Sawada et al. | 250/222.2 |
| 6,267,016 B1 * | 7/2001 | Call et al. | 73/863.22 |
| 6,471,751 B1 * | 10/2002 | Semanderes et al. | 95/271 |
| 6,508,864 B2 * | 1/2003 | Day | 95/219 |
| 6,520,034 B1 * | 2/2003 | Masquelier et al. | 73/863.21 |
| 7,125,437 B2 * | 10/2006 | Bryden et al. | 95/29 |
| 2002/0078826 A1 | 6/2002 | Day | |

FOREIGN PATENT DOCUMENTS

| | | |
|---|---|---|
| DE | 2004808 | 10/1970 |
| DE | 3428539 | 2/1986 |
| EP | 0597786 | 5/1994 |
| JP | 63224754 | 9/1988 |
| SU | 558710 | 5/1977 |
| WO | WO 89/10795 | 11/1989 |

OTHER PUBLICATIONS

Abstract of Japanese Patent Document No. 2003053308 (Feb. 25, 2003).
Abstract of Russian Patent Document No. 2092247 (Oct. 10, 1997).
Abstract of Soviet Patent Document No. 800534 (Jan. 30, 1981).
Abstract of Japanese Patent Document No. 63224754 (Sep. 19, 1988).
Abstract of Japanese Patent Document No. 2003053308 (Feb. 25, 2003).
Abstract of Russian Patent Document No. 2092247 (Oct. 10, 1997).
Abstract of Russian Patent Document No. 2115485 (May 6, 1997).
Abstract of Soviet Patent Document No. 800534 (Jan. 30, 1981).

* cited by examiner

APPARATUS FOR COLLECTING PARTICLES

CROSS REFERENCE TO RELATED APPLICATIONS

This application is the U.S. national phase of International Application No. PCT/GB2004/000251 filed on Jan. 21, 2004 and published in English on Aug. 5, 2004 as International Publication No. WO 2004/065017 A2 which application claims priority to Great Britain Application No. 0301257.2 filed on Jan. 21, 2003, the contents of which are incorporated by reference herein.

The present invention generally concerns improvements to apparatus for collecting airborne particles. The present invention is particularly, although not exclusively, directed to apparatus for the collection of particles from an environment in which the temperature of ambient air is close to or even below 0° C.

The separation of particles from air is often achieved by the use of cyclones that provide for rapid acceleration of the air whereby differential centripetal forces act to dislodge particles from the airflow. The collection of the separated particles, for example, for analysis, often requires that the particles be suspended in a minimum volume of a collection fluid, normally water. Apparatus providing this facility often employ an injection of water, from a reservoir associated with the cyclone, into the airflow within the cyclone body and/or the wetting of the cyclone body walls. Such apparatus may, for example, sample about 700 liters of air per milliliter of water.

A particular problem of these apparatus lies in the fact that, under certain environmental conditions, the small volume of injected collection fluid is susceptible to freezing through contact with a large volume of cold air passing into the cyclone body. In addition, where the apparatus is exposed to prolonged ambient cold, the collection fluid may also freeze within the reservoir.

Freezing of the collection fluid prevents the correct operation of the collection system and analysis of the type and concentration of particles in an environment. The problem therefore represents a severe limitation to the operation of these apparatus in circumstances where there is a need to identify pathogenic threats in environments in which the temperature is close to or below 0° C.

One approach to the problem utilises a heater to heat the environment immediately ambient the apparatus. However, this approach is generally unsatisfactory especially where there is an urgent need to begin operation of an apparatus having had prolonged contact with a freezing environment.

Alternative approaches to the problem may provide antifreeze to the collection fluid or, additionally or alternatively, heat one or more of the cyclone body, reservoir and connecting lines. For example, WPI abstract accession no. 1988-304531 discloses a cyclone separator dust collecting vessel having an electric heater for heating the wall surfaces of the vessel. However, these approaches are complicated by problems involving sample integrity and analysis and the need to reengineer the cyclone or apparatus. In addition, heating of the cyclone body, reservoir and connecting lines may not adequately prevent freezing of the relatively low volume of injected collection fluid through contact with the large volume of cold air entering the cyclone.

WPI accession nos. 1998-249380 and 2000-021641 disclose cyclones for cleaning atmospheric air having staged or tiered air intake chambers in the body of the cyclone and heated gas manifolds for heating the air intake. The heating of the intake air prevents condensation of water vapour and the formation of ice.

WPI accession no. 1981-79247 discloses a gas scrubber comprising a cyclone and secondary dust separator. The dust separator is enclosed in a housing, which forms a heating cavity for the dust separator.

The present invention, however, generally seeks to overcome the problem of freezing of injected collection fluid, by providing more efficient means for heating air entering the cyclone.

Accordingly, the present invention provides apparatus for collecting particles from air, comprising a cyclone having air inlet and outlet means, means maintaining an airflow there through and means delivering a collection fluid from a reservoir to particles in or separated from the airflow in the cyclone, in which the air inlet means is associated with means for heating the incoming air.

The term "air inlet means", as used in this specification, includes any arrangement providing for the passage of air from the environment to the cyclone body. For example, the air inlet means may comprise an elevated, annular air intake slot with connecting means, for example tubing, guiding the air to the cyclone body.

It will be understood, therefore, that the present invention includes within its scope heating means arranged on, within or around the air inlet means and, in particular, the intake slot and/or connecting means.

In some embodiments of the present invention, the heating means is co-axially mounted on or within the air inlet means. Preferably, the heating means is maintained in thermal contact with a portion of an exterior or interior surface of the air inlet means. The heating means may be mounted to the air inlet means so that, at least a portion of, their surfaces are touching. However, it will be apparent that a thermally conductive intervening element may also be provided between these surfaces. Of course, in these embodiments the air inlet means will, at least in part, be thermally conductive.

The air inlet means may comprise any suitable thermally conductive material such a metal or metal alloy. A suitable material comprises an aluminium alloy known by the British Standard, BS1474 6082T6.

Alternatively, the heating means may be co-axially mounted within the air inlet means so as to heat the incoming air in the air inlet means directly. Preferably, the heating means is not in contact with the air inlet means. In some embodiments, therefore, the air inlet means may comprise a heat insulating material.

The heating means may comprise any suitable heating means and may, in particular, may be powered by a battery or other means. In a preferred embodiment, the heating means comprises a heating block, which is mounted in thermal contact with a thermally conductive portion of a cylindrical air inlet tube. The block, which may be, for example, semicircular in cross section, may thermally contact part or the whole of the circumferential surface of the portion.

The heating block may comprise a metal or metal alloy as well as one or more heating elements, such as those known to the art as "fire rods". Preferably, the heating block comprises a brass, for example that known by the British Standard, BS2874 C2121M. However, other thermally conductive materials and heating elements may also be suitable for the practice of the invention.

The heating block may be mounted on or within the air inlet means by any suitable mounting means. In a preferred embodiment, the heating block is configured to slide or clamp onto the air inlet tube. The mounting means may additionally or alternatively, comprise abutments or indentations on the outer surface of the air inlet means. Such arrangements enable the heating block to be located at any suitable or convenient position on the air inlet tube.

It will be understood that in the preferred embodiment, the material, dimensions and number of heating rods of the heating block will be chosen to optimise heat transfer having regard to the contact time of the incoming air and other considerations such as power consumption, weight and convenient handling.

In one embodiment, therefore, in which the air inlet means comprise an aluminium alloy (BS 1474 6082T) tube of internal diameter 25.4 mm, the cylindrical brass (BS2874 C2121M) heating block includes 4 fire rods rated at 235 W and has length 130 mm, internal diameter 38 mm (mass 3.8 kg). Good results are obtained for cyclone air intake velocities ranging from 500 to 800 L/min.

The heating block may, however, be comprised by a plurality of segments including, for example, a half cylindrical surface in an upper surface thereof, which are arranged around the air inlet tube by mounting means. A preferred heating block comprises our brass (BS2874 C2121M) segments, each defining a half-cylindrical surface and including two fire rods rated at 110 W. The brass segments are fixed to mounting means comprising a casing, formed from two hinged members so that on closure of the casing the segments define a heating block of cylindrical length 230 mm (mass ~10 kg). The mounting means include screw clamp arrangements associated with each box member which enable the heating block to be located in any suitable position on the air inlet tube.

Thus, an aspect of the present invention provides a heating block assembly for heating an air inlet tube, comprising a plurality of heating block segments including a half-cylindrical surface in an upper surface thereof and mounting means for mounting the segments to the air inlet tube, in which the mounting means comprise hinged box members defining means for receiving the segments whereby closure of the casing places the half cylindrical surface of each segment in contact with the outer surface of the air inlet tube.

The heating means may alternatively or additionally comprise means delivering air exiting the cyclone to the air inlet means. The exhaust air, which may be solely heated by the cyclone motor, or include an additional component from, say, the heating block may, for example, be delivered to an outer or inner tube surrounding or within the air inlet means before exiting the apparatus. Alternatively, the exhaust air may simply be delivered to a portion of an outer surface of the air inlet means.

The heating means may be associated with a temperature sensor for sensing the temperature of heated air entering or exiting the cyclone. Preferably, the heating means is associated with control means responsive to the temperature sensor whereby to control the extent of heating of the block required to prevent injected collection fluid from freezing. The temperature sensor may comprise an ordinary bimetallic strip thermocouple.

In a preferred embodiment of the present invention, the temperature sensor comprises a voltage-output thermocouple, such as a type K thermocouple, and the control means compares the output voltage with a reference voltage whereby to actuate heating when, for example, the output voltage falls below the reference voltage. The arrangement allows fine and safe control of heating of the block and optimal power consumption and even temperature control of the air in the cyclone body as the ambient temperature drops.

In some embodiments of the present invention, the apparatus also comprise means for warming or heating the fluid collection reservoir and/or cyclone body. This second heating means may simply comprise means for trapping the exhaust air or heat from or the exhaust air.

The second heating means may therefore comprise enclosure means enclosing, at least in part, one or more of the fluid collection reservoir, cyclone body and air outlet means. Preferably, the enclosure means does not enclose the first heating means in which case the heating block, for example, is protected by a weatherproof container or jacket.

In some embodiments, however, the second heating means may compliment the first heating means. In particular, exhaust air delivered to the air inlet means may be trapped by an enclosure also enclosing a portion, preferably a major portion, of the air inlet means. It will be apparent, however, that, in all embodiments of the present invention, at least a portion of the air inlet means will not be enclosed.

In another preferred embodiment of the present invention, the enclosure means comprise a rigid, box container equipped with closure means. However, other enclosure means, including framework structures supporting removable panels and/or insulating fabrics, may also be suitable.

As mentioned above, the enclosure means may enclose only part of the air outlet means so that only a portion of the heated air exiting the cyclone may be retained within the enclosure means. Alternatively, the enclosure means may not enclose the air outlet means and a portion of the heated air exiting the cyclone may be delivered to the enclosure means.

Preferably, however, the enclosure means wholly encloses the air outlet means and includes ventilation means, allowing ingress of ambient air and exit of heated air. The movement of ambient air into the enclosure prevents overheating of the sample and/or apparatus.

The ventilation means may simply comprise slots or apertures provided in, for example, the rigid box container. Preferably the ventilation means comprise louvres or slats which may, optionally, be rotatably mounted. The ventilation means may further comprise one or more blowers to assist in the movement of ambient air.

The ventilation means may also be controlled by second control means. In one embodiment, the enclosure means include one or more temperature sensors for sensing the temperature of the trapped air. In this embodiment, the second control means may be responsive to the temperature sensor or sensors so as to actuate, for example, the blowers.

The present invention substantially prevents freezing of injected collection fluid at ambient temperatures approaching −15° C. and offers the advantage that particles may be rapidly sampled and analysed even after prolonged contact of the apparatus with freezing cold.

The invention further offers the advantage that existing particle collection apparatus are easily modified without the need for reengineering the apparatus. The incorporation of simple heating apparatus on or within the air inlet means avoids the need for antifreeze and provides an efficient and portable solution to the problem of freezing collection fluid on injection.

In addition, the retention of warm air, heated by the first heating means (and the cyclone motor), by simple enclosure means provides a cheap and portable solution to the problem of freezing of collection fluid in the reservoir. The present invention therefore avoids the necessity to heat air immediately ambient the apparatus and allows deployment of the whole apparatus outside an artificial environment, such as that provided by a heated vehicle. Further, the invention provides a heating solution for the collection fluid in which the integrity of the sample in the cyclone body is not prejudiced by, for example, excessive heat.

The present invention will now be described with reference to several embodiments and the following examples and drawings in which.

Figure 1:
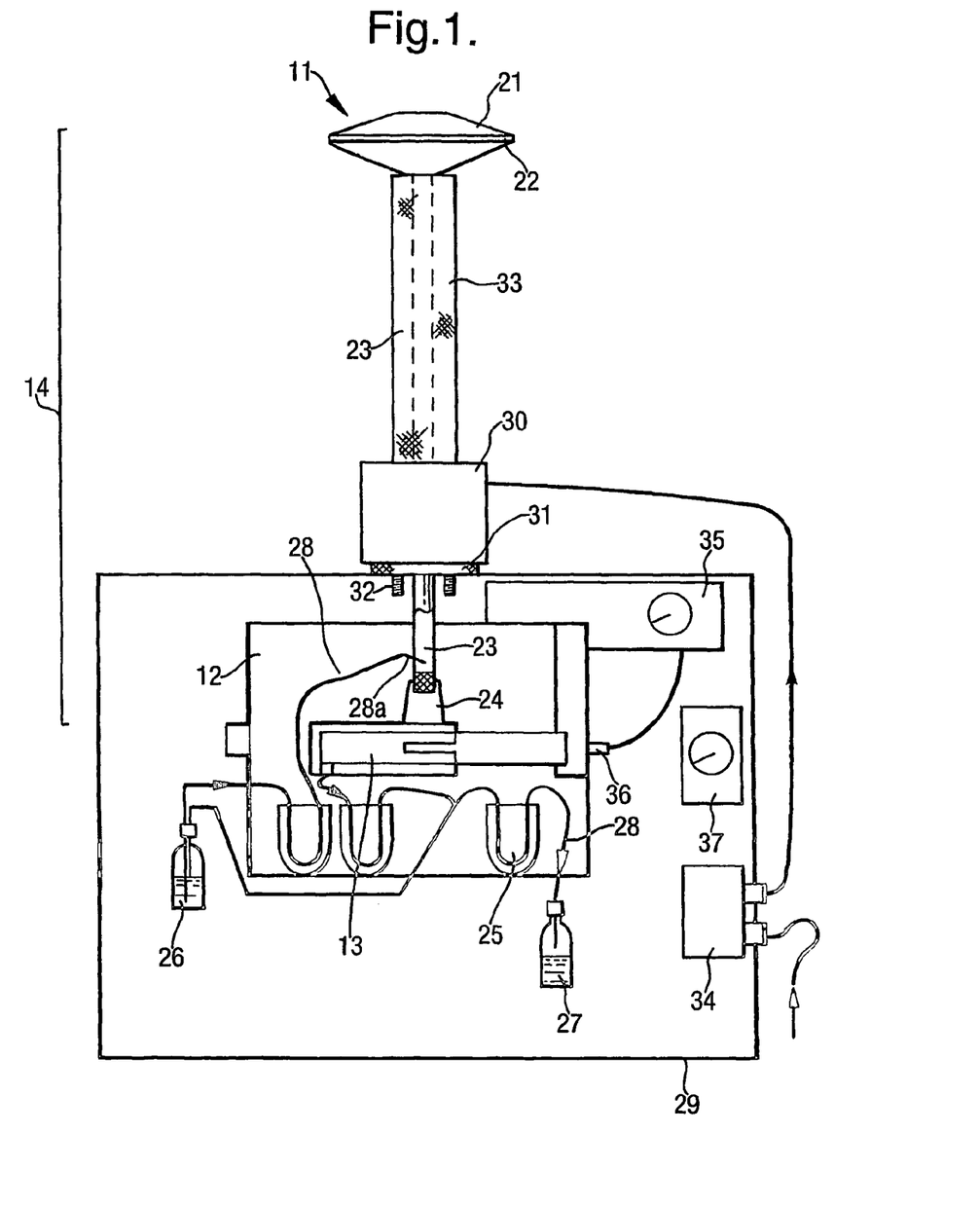
FIG. 1 is a section view of the apparatus of one embodiment of the present invention.
Figure 2:
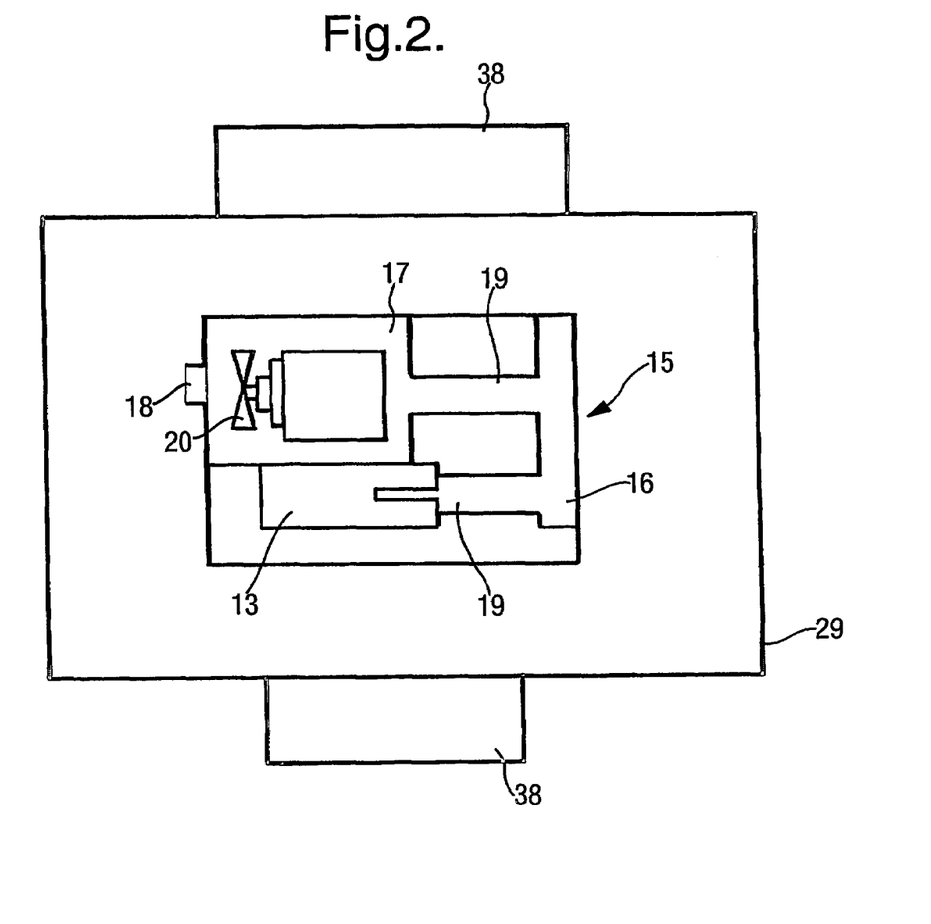
FIG. 2 is a part, plan section view of the embodiment of FIG. 1.

Having regard now to FIGS. 1 and 2, a low temperature, particle collection apparatus, generally designated 11, comprises a support member 12 housing a cyclone 13 having air inlet means, generally designated, 14 and air outlet means, generally designated, 15.

The air outlet means 15 comprise chambers 16, 17 provided in the support member 12, connecting the cyclone body 13 to an aperture 18 by tubes 19. One chamber 16 comprises a plenum chamber whilst the other houses a motor driven blower 20, which moves air from the air inlet means 14 through the cyclone body 13 towards the aperture 18.

The air inlet means 14 comprise a detachable, lozenge-shaped element 21 having an annular slot 22. The slot 22 admits air into a connecting tube 23 connecting the lozenge 21 with a tapered tube 24 entering the cyclone body 13. The tapered and connecting tubes 23, 24 are connected by a nut and screw arrangement.

The support member 12 also houses a number of peristaltic pumps 25 in fluid communication with a first reservoir 26 and a second, reserve reservoir 27. The first reservoir 26 contains an aqueous buffer solution, which is supplied, via tubing 28 and inlet tube 28a, to the airflow in the connecting tube 23 just above the cyclone body 13 and from the cyclone body 13 back to reservoir 26. Although sample collection is cyclic, leading to a more concentrated sample for analysis, the system includes a T-joint in tubing 28 enabling a portion of the sample-started. The temperature of the air inlet tube and heating block and the temperature of air exiting the cyclone, and air in the enclosure was monitored. After about 15 minutes the temperature of the air in the enclosure had risen to about 15° C. The water reservoir was installed to the apparatus and continuous sampling begun.

Figure 3A:
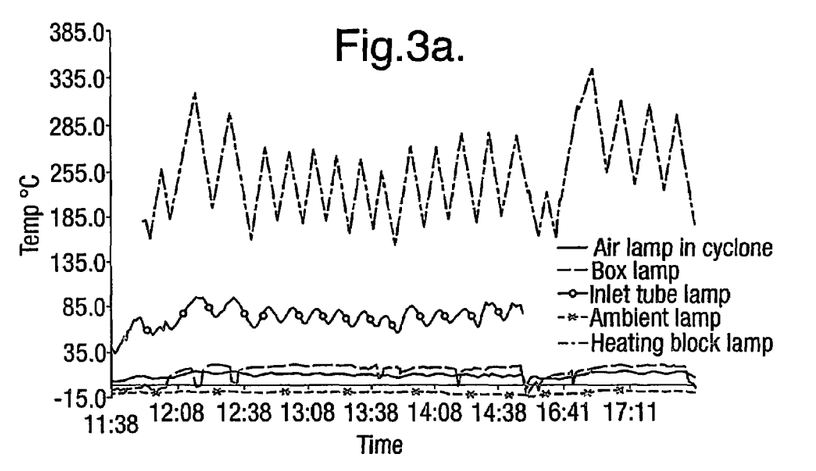
FIGS. 3a) and b) are graphs showing the temperatures of various parts of the apparatus of FIG. 1 during operation at ambient temperatures of −9° to −12° C.
Figure 3B:
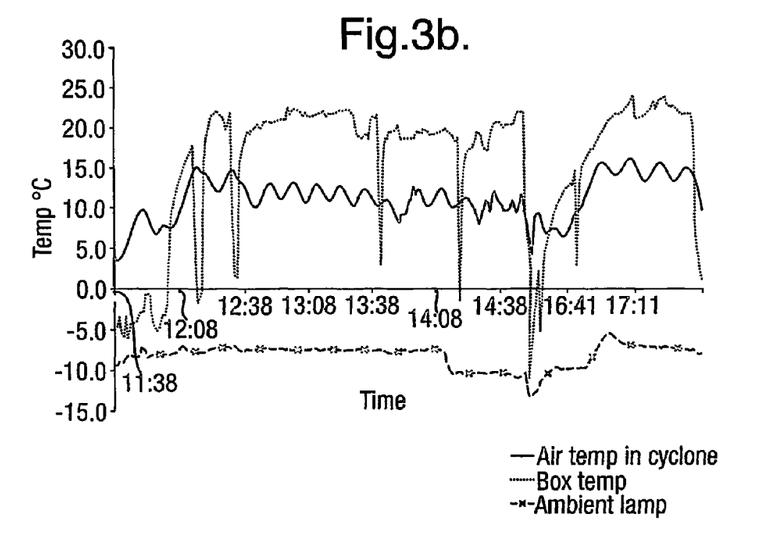

FIGS. 3a and 3b show the variation in the temperature of the heating block, inlet tube temperature, enclosure and air temperature in the cyclone during sampling. The heating block and control means was found to maintain the temperature of air exiting the cyclone at 10 to 13° C. during a period of 2 hours. The sudden drops in the temperature of the enclosure (FIG. 3b) are due to the opening of the enclosure to install further collection fluid. It was noted that the second control means preventing overheating in the enclosure did not activate during the run, the temperature of enclosed air not exceeding 24° C.

EXAMPLE 5

The apparatus of FIG. 1 without a reservoir, was acclimatised to a climatic test chamber at an ambient temperature of −12° C. When the temperature of the apparatus had fully equilibrated with ambient temperature, the cyclone was started. After about 15 minutes the temperature of the air in the enclosure had risen to about 15° C. The water reservoir was installed to the apparatus and continuous sampling begun. FIG. 3 shows the variation in temperature of air exiting the cyclone and enclosed air during sampling over a period of 30 minutes. It was noted that the second control means did not activate during the run, the temperature of the enclosed air not exceeding 24° C.

Figure 4:
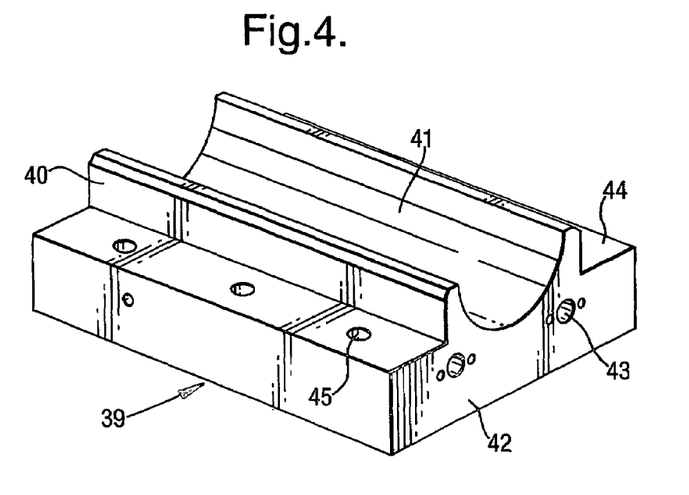
FIG. 4 is a perspective view of a heating block segment forming part of a preferred embodiment of the present invention.
Figure 5:
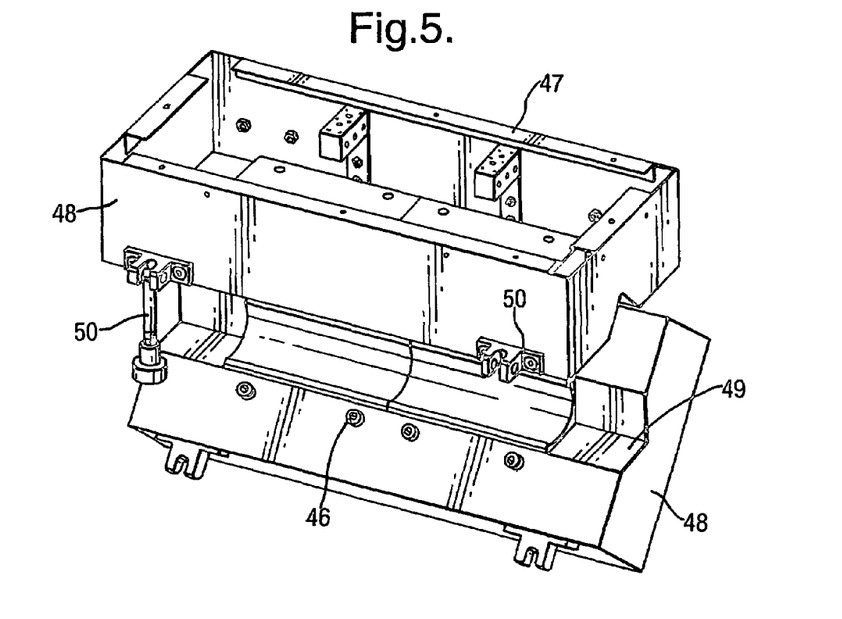
FIG. 5 is a part cut-away perspective view showing an assembly for mounting a heating block comprising the segments of FIG. 4 to air inlet means.

Referring now to FIGS. 4 and 5, a preferred heating block, for use with apparatus similar to that shown in FIG. 1, comprises four, generally rectangular, brass segments 39.

The upper surface of each segment 39 includes raised portions 40, oppositely disposed to one another and extending along the longitudinal length thereof. Opposing side surfaces of raised portions 40 and a portion of the upper surface there between together define a centrally disposed half-cylindrical surface 41 for contacting the air inlet tube 23.

A side surface 42 of each segment 39 provides longitudinally extending apertures 43 for receipt of the fire rods (not shown). Upper and lower surfaces adjacent raised portions 40 define generally rectangular side portions 44 in which a series of apertures 45 are provided for receipt of screw elements 46 for fixing each segment 39 to a casing.

Casing, generally designated, 47 comprise two hinged, generally rectangular box members 48 each providing surfaces defining a longitudinal channel 49 and cavities for receipt of side portions 44 of segments 39. The surfaces of each box member 48 contacting side portions 44 are provided with threaded apertures allowing fastening thereof through the screw elements 46.

Longitudinal outer side surfaces of each box member 48 are equipped with screw clamp means 50 disposed at or adjacent each end (one screw not shown [ ]). Closure of the casing 47 and fastening of the clamp means 50 secures the half cylindrical surface 41 of each heating segment 39 opposite each other and in contact with the outer circumferential surface of the air inlet tube 23.

Figure 6A:
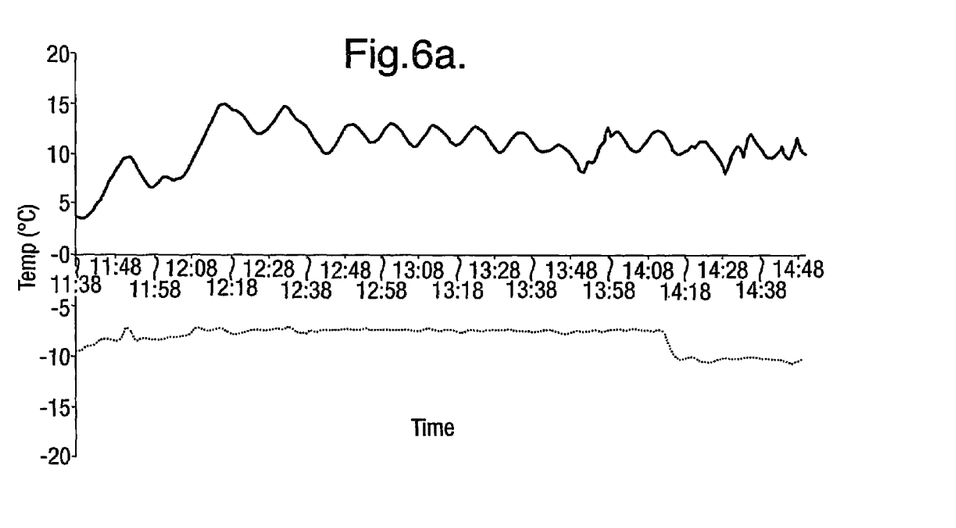
FIGS. 6a) and b) are graphs indicating the temperature of air in the cyclone body for, respectively, the embodiment of FIG. 1 and another embodiment in which the temperature sensor is a output voltage thermocouple.

FIG. 6a) shows the variation in air temperature in the cyclone body during cooling of ambient air in apparatus similar to that of FIG. 1. The heating block comprises a single cylindrical block (longitudinal length 130 mm, mass 3.8 kg, four fire rods rated at 235 W) described above and the thermal control means is responsive to a single temperature sensor based on an ordinary bimetallic strip thermocouple.

Figure 6B:
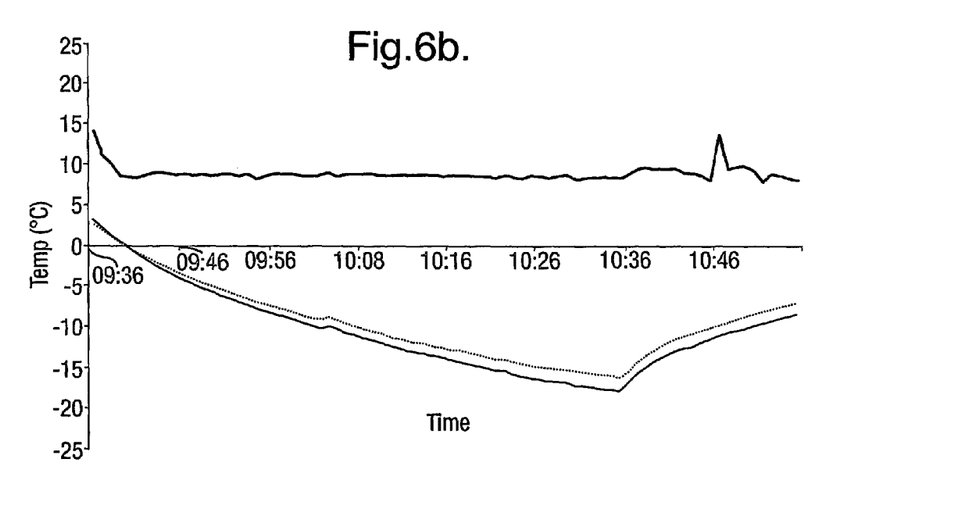

FIG. 6b) shows the variation in air temperature in the cyclone body during cooling of ambient air in apparatus similar to that of FIG. 1. The heating block is comprised of four heating segments 39 (longitudinal length 230 mm, mass ~10 kg, eight fire rods rated at 110 W) described above and the thermal control means is responsive to a more sensitive temperature sensor comprising an output-voltage thermocouple (as mentioned previously).

The apparatus are operated at substantially similar flow rates—ranging from 500 to 800 L/min and the temperature sensors each monitor the temperature of the air exciting the cyclone body. As may be seen from FIG. 6a), there is significant temperature fluctuation in the air temperature in the cyclone body (upper line)—even when the temperature of ambient air is approximately constant (lower line). By contra as may be seen from FIG. 6b), the longer heating block and the more sensitive temperature sensor leads to an air temperature in the cyclone body (upper line) which is constant—even where the ambient temperature falls (to −16° C.).

The invention claimed is:

1. Apparatus for collecting particles from air, comprising a cyclone having air inlet and outlet means and a body, means maintaining an airflow there through and means delivering a collecting fluid from a reservoir to particles separated from the air flow in the cyclone, in which the air inlet means is associated with means for heating the incoming air, and means for enclosing, at least in part, the air outlet means and at least one of the cyclone body or reservoir, so as to trap at least a portion of the heated air.

2. Apparatus according to claim 1, in which the heating means is in thermal contact with at least a portion of an exterior surface of the air inlet means.

3. Apparatus according to claim 2, in which the heating means comprise a heating block having one or more heating elements.

4. Apparatus according to claim 3, in which the heating block is configured so as to clamp or slide onto the air inlet means.

5. Apparatus according to claim 3, in which the heating block comprises a metal or metal alloy.

6. Apparatus according to claim 1, in which the heating means is associated with control means responsive to sensing means sensing temperature of air entering or exiting the cyclone.

7. Apparatus according to claim 1, in which the enclosure means comprise a rigid container having closure means.

8. Apparatus according to claim 1, in which the enclosure means comprises ventilation means.

9. Apparatus according to claim 8, in which the ventilation means comprises a louvre.

10. Apparatus according to claim 8, in which the ventilation means further comprises a blower.

11. Apparatus according to claim 10, in which the blower is associated with second control means responsive to sensing means sensing temperature within the enclosure means.

* * * * *